United States Patent [19]

Chan et al.

[11] Patent Number: 5,804,420
[45] Date of Patent: Sep. 8, 1998

[54] PREPARATION OF RECOMBINANT FACTOR VIII IN A PROTEIN FREE MEDIUM

[75] Inventors: Sham-Yuen Chan, El Sobrante; Kathleen Harris, Oakland, both of Calif.

[73] Assignee: Bayer Corporation, Berkeley, Calif.

[21] Appl. No.: 844,714

[22] Filed: Apr. 18, 1997

[51] Int. Cl.$^6$ .............................. C12N 5/02; C12N 5/10; C12N 15/12; C07K 14/755
[52] U.S. Cl. ..................... 435/69.6; 435/325; 435/404; 530/383
[58] Field of Search .......................... 435/69.6, 172.3, 435/325, 352, 363, 373, 383, 404, 358, 369; 530/383; 935/33, 34

[56] References Cited

U.S. PATENT DOCUMENTS

| 5,024,947 | 6/1991 | Inlow | 435/404 |
| 5,378,612 | 1/1995 | Nakashima | 435/69.6 |

*Primary Examiner*—Dian C. Jacobson
*Attorney, Agent, or Firm*—James A. Giblin; Michael J. Beck

[57] ABSTRACT

Recombinant Factor VIII can be produced in relatively large quantities on a continuous basis from mammalian cells in the absence of any animal-derived proteins such as albumin by culturing the cells in a protein free medium supplemented with polyol copolymers, preferably in the presence of trace metals such as copper. In very preferred embodiments, the medium includes a polyglycol known as Pluronic F-68, copper sulfate, ferrous sulfate/EDTA complex, and salts of trace metals such as manganese, molybdenum, silicon, lithium and chromium.

12 Claims, No Drawings

PREPARATION OF RECOMBINANT FACTOR VIII IN A PROTEIN FREE MEDIUM

BACKGROUND OF THE INVENTION

1. Field: This disclosure is concerned generally with the manufacture of recombinant Factor VIII and specifically with the manufacture of recombinant Factor VIII in a serum or protein free medium.

2. Prior Art: Hemophilia A is an X-linked recessive genetic disorder that is due to a defective or deficient Factor VIII molecule, resulting in a hemorrhagic tendency. To control bleeding episodes, hemophiliacs are treated with Factor VIII. Historically Factor VIII has been isolated from human blood plasma. However, therapy with plasma-derived Factor VIII has been associated with transmission of several human viruses, such as hepatitis and human immunodeficiency viruses.

With the advent of recombinant DNA technology, the structure of human Factor VIII and its gene has been elucidated. The transcription product of the gene, which is derived from 26 exons, is a messenger RNA molecule of ~9000 bases in length, coding for a large protein of 2351 amino acids. Structural studies of Factor VIII indicate that it is a glycoprotein containing a significant number of carbohydrate residues.

The cDNA coding for Factor VIII has been cloned and stably expressed in baby hamster kidney (BHK-21) and Chinese hamster ovary (CHO) cells. Commercial processes have been developed to produce recombinant Factor VIII for treatment of hemophilia A. Recombinant Factor VIII is currently manufactured by genetically engineered mammalian cells, thus obviating the reliance on plasma and minimizing any possible risk of virus transmission.

Gene amplification has been the method of choice to derive high production cell lines for therapeutic proteins. The amplification strategy involves the linking of a transcriptional unit encoding the desired protein to an amplifiable marker such as dihydrofolate reductase. Transfection techniques are then applied to transfer the vector DNA to recipient cells. Cell populations are selected for increased resistance to the drug of choice such as methotrexate. The establishment of a stable cell clone is accomplished by limiting dilution cloning. These cell clones are then adapted to a serum-free production medium and monitored for production of the desired protein.

For labile proteins such as Factor VIII, human albumin has been added as a stabilizer during the preparation and purification procedures. Although the albumin is subjected to a viral inactivation step by pasteurization, it would be ideal if recombinant Factor VIII could be manufactured in the complete absence of human and animal blood proteins. I have now found this is possible by using a novel cell culture medium. Details are described below.

SUMMARY OF INVENTION

The method for the continuous production of relatively large quantities of recombinant Factor VIII (rFVIII) from mammalian cells in the absence of any human or animal-derived plasma proteins comprises culturing the mammalian host cells in a protein-free medium supplemented with a polyol polymer such as Pluronic F-68. The preferred medium includes copper sulfate, a ferrous sulfate/EDTA complex, and the salts of trace metals such as manganese, molybdenum, silicon, lithium, and chromium.

DETAILED DESCRIPTION OF THE INVENTION

Recent advances in recombinant protein expression technology have made possible the production of protein in large quantities in mammalian cells. Host cells suitable for Factor VIII production include cell lines such as baby hamster kidney (BHK) cells, Chinese hamster ovary (CHO) cells, and human embryonic kidney (HEK) cells. Particularly preferred are baby hamster kidney cells, specifically those transfected with a gene capable of directing the expression of Factor VIII as described in Wood et al. (1984) (including derivatives such as clonal variants and progeny thereof). Such a cell line has been deposited with the American Type Culture Collection and has been assigned the accession number ATCC CRL-8544.

The desired host cell line carrying the Factor VIII gene is typically adapted to grow as suspension cultures in a protein-free production medium which is supplemented with lipoprotein. The basal medium chosen for culturing the host cell line is not critical to the present invention and may be any one of, or combination of those known to the art which are suitable for culturing mammalian cells. Media such as Dulbecco's Modified Eagle Medium, Ham's Medium F-12, Eagle's Minimal Essential Medium, and RPMI-1640 Medium, and the like, are commercially available. The addition of growth factors such as recombinant insulin is conventional in the art.

Due to the labile nature of Factor VIII, the productivity of the engineered host cells is severely reduced under protein-free conditions. Human serum albumin is commonly used as a serum-free culture supplement for the production of recombinant proteins. Human serum albumin serves many functions including: (1) as a carrier for fatty acids, cholesterol and lipophilic vitamins, steroid hormones and growth factors; (2) as a protective agent against damages due to shear forces; (3) as a buffer for pH changes; and (4) as an osmotic pressure regulator. Another critical role of albumin is perhaps to protect labile proteins such as Factor VIII from proteolysis by serving as a substrate for proteases.

The impurities present in albumin preparations may also contribute to the stabilizing effect of albumin. Factors such as lipoprotein (Chan, 1996) have been identified as a replacement for human serum albumin for the production of recombinant Factor VIII under serum-free conditions.

Our attempt to develop a production medium free of human plasma-derived albumin led to the invention of this disclosure, a basal protein-free medium for recombinant Factor VIII production. The preferred medium consists of modified Dulbecco's Minimum Essential Medium and Ham's F-12 Medium (50:50, by weight) supplemented with recombinant insulin (Nucellin, Eli Lilly) at 10 $\mu$g/ml, and $FeSO_4$·EDTA (50 $\mu$M). With the exception of Factor VIII production, engineered BHK cells grow well in this protein-free basal medium.

Surprisingly, the addition of a polyol such as Pluronic F-68 had no effect on growth but enhanced the specific productivity of the BHK cells for Factor VIII. Serendipitously, the addition of copper sulfate further enhances the production of Factor VIII. Also the inclusion of a panel of trace metals such as manganese, molybdenum, silicon, lithium, and chromium lead to further increases in Factor VIII production. A continuous process was then developed for Factor VIII production under human plasma-derived protein-free conditions. Further information regarding the use of Pluronic polyols can be found in Papoutsakis (1991) and Schmolka (1977).

Pluronic F-68, a polyglycol, (BASF, Wyandot) is commonly used to prevent foaming that occurs in stirred cultures, and to protect cells from shear stress and bubble damage in sparged cultures. Pluronic F-68 is a nonionic block copolymer with an average molecular weight of 8400, consisting of a center block of poly(oxypropylene) (20% by weight) and blocks of poly(oxyethylene) at both ends. Extensive research on the role of Pluronic F-68 indicates that Pluronic F-68 acts as a surfactant and prevents damage to cells by allowing the drainage of cells away from bubbles formed in the bioreactors during stirring or sparging. However, several investigators have noticed beneficial effects of Pluronic F-68 on growth under culture conditions in which shear is minimal (Mizrahi, 1975; Murhammer and Goochee, 1990). Co-purification of lipids with Pluronic F-68 during product purification provides anecdotal evidence that the Pluronic polymer may substitute for albumin not only as a surfactant, but may also act as a carrier for lipids. Pluronic F-68 may also prevent membrane damage from killing cells before repair can be effected, possibly by direct intercalation into the membrane. The role of Pluronic F-68 in acting as a metal ions buffer is completely unknown.

Although there are reports that Pluronic F-68 in media can increase volumetric productivity, the mechanism of action appears to be maintenance of cell viability (Schneider, 1989; Qi, 1996). To our knowledge, this is the first time that Pluronic F-68 has been seen to increase specific production of a particular protein product. Since viabilities and growth rates are comparable in our system with and without Pluronic F-68, maintenance of cell viability cannot be the mechanism of action of Pluronic F-68 in our system. However, the effect of Pluronic F-68 addition is immediate and dramatic, whatever the mechanism.

It is anticipated that a range of other polyols would have similar effects. Such other polyols include nonionic block copolymers of poly(oxyethylene) and poly(oxypropylene) having molecular weights ranging from about 1000 to about 16,000.

In addition to conventional suspension culturing techniques such as shake flasks, spinner flasks, and roller bottles, the method of the present invention is also applicable for use withperfusion and batch bioreactors. Following culturing the host cells, the Factor VIII may be recovered from the spent medium by standard methodologies such as ultrafiltration or centrifugation. If desired, the recovered Factor VIII may be purified by, for example, ion exchange or size exclusion chromatography, immuno-affinity or metal chelate chromatography, and the like.

As used herein, a "human or animal protein-free medium" is a cell culture medium which is free of any protein that has been derived from a human source or an animal source. Proteins which are isolated from human or animal sources inherently carry the risk of introducing viral contamination. The goal of a human or animal protein-free medium is thus to eliminate or at least greatly reduce the risk of viral transmission.

Example 1: Baby hamster kidney (BHK-21) cells transfected with a gene capable of directing the expression of Factor VIII were obtained from Genentech, Inc., South San Francisco, Calif., U.S.A. The cell line was prepared as described in detail in Wood et al. (1984) and was deposited with the American Type Culture Collection and given accession number ATCC CRL-8544. A clonal variant of this cell line was also obtained from Genentech, Inc., and used in all examples.

The BHK-21 cells containing the gene encoding Factor VIII were cultivated as suspension cultures in shake flasks using a serum-free basal medium containing the following: Ham's F-12 Medium and Dulbecco's Minimal Essential Medium (50:50, by weight), Nucellin (recombinant insulin, 5–10 $\mu$g/ml), $FeSO_4$.EDTA (50 $\mu$M), and $MgCl_2$ (15 mM). Cells were maintained and passaged at 48 hour intervals. Cells were spun down at 800×g for 5 minutes, counted and re-seeded at a density of $1\times10^6$ cells per ml. Each flask contains 50–100 ml of fresh medium. The shake flasks were placed on a rotator, incubated at 37° C., and maintained as suspension culture by swirling gently between 90–110 r.p.m. The effect of a polyol such as Pluronic F-68 (0.1%), shown as F-68 below, and copper sulfate (50 nM) on Factor VIII production was examined in shake flasks. Factor VIII was quantitated by a chromogenic assay. The assay is sold commercially as a test kit known as Coatest VIII:C/4 and is available from Baxter HealthCare Products. The cells were maintained by this procedure for 24 days. The Factor VIII activity in each medium, as determined with the Coatest VIII:C/4 kit, is shown in Table 1.

TABLE 1

| Conditions | Titer (U/ml) | Specific Productivity ($\mu$U/cell/day) | % Increase over basal |
|---|---|---|---|
| Basal Medium | 0.15 ±0.07* | 0.026 ±0.013 | 0 |
| Basal + F-68 (0.1%)** | 0.24 ±0.04 | 0.052 ±0.013 | 200 |
| Basal + F-68 (0.1%) + Cu (50 nM**) | 0.42 ±0.09 | 0.091 ±0.013 | 350 |

*Mean of 36 samples ± standard deviations. The cells were monitored for Factor VIII production over a period of 24 days as described above.
**Titration experiments showed that 0.1% is the optimal dose for Pluronic F-68. Increasing the concentration to 0.3% had no significant impact on Factor VIII production. Dose-response experiments revealed that 50–800 nM copper sulfate is optimal for Factor VIII production.

As shown in Table 1, the addition of Pluronic F-68 alone or, preferably, in combination with copper sulfate significantly enhanced the titer and specific productivity of BHK cells containing the gene encoding Factor VIII under protein-free conditions.

Example 2: To further optimize the production of Factor VIII under protein-free conditions, trace metals were added to the protein-free production medium. Factor VIII production was then assessed by the continuous shake flask culture system as described in example 1 for 16 days. The data is shown in Table 2. In the absence of copper sulfate, the trace metals had no effect on Factor VIII productivity. See Table 2.

TABLE 2

| Conditions | Titer (U/ml) | Specific Productivity ($\mu$U/cell/day) | % Increase over basal + F-68 |
|---|---|---|---|
| Basal + F-68 | 0.46 ±0.11 | 0.065 ±0.013 | 0 |
| Basal + F-68 + Cu | 0.53 ±0.15 | 0.078 ±0.026 | 120 |
| Basal + F-68 + Cu + metals* | 0.73 ±0.16 | 0.104 ±0.026 | 160 |

*Metals include $CuSO_4.5H_2O$ (50 nM), $MnSO_4$ (3 nM), $Na_2SiO_3.9H_2O$ (1.5 $\mu$M), $[NH_4]_6Mo_7O_{24}.4H2O$ (3 nM), $CrK(SO_4)_2.4H_2O$ (1.5 nM), and LiCl (236 nM).

Example 3: The effect of trace metals and copper on factor VIII production was further evaluated in a perfusion fermenter. Two 1.5-liter fermenters were seeded with the BHK clonal variant at a density of $2\times10^6$ cells/ml using the basal medium described in Table 1. The fermenter was perfused at a rate of 0.5 liter/day. One fermenter was kept as a control and the other fermenter was supplemented with copper and trace metals as described in Table 2. The fermenters were maintained for 15 days with an average cell density of ~2–3×10⁶ cells/ml. As shown in Table 3, the addition of Pluronic F-68, copper, and trace metals significantly enhanced the specific productivity of BHK cells harboring the gene encoding factor VIII under protein-free conditions under continuous perfusion conditions. This production method can be fermenters (200 to 500 liter) equipped with cell retention devices such as settlers.

TABLE 3

| Days | Specific Productivity (μU/cell/day) | |
|---|---|---|
| | Basal Medium | Cu + metals |
| 1 | 0.02 | 0.04 |
| 2 | 0.02 | 0.05 |
| 3 | 0.02 | 0.045 |
| 4 | 0.018 | 0.05 |
| 5 | 0.02 | 0.05 |
| 6 | 0.035 | 0.060 |
| 7 | 0.025 | 0.055 |
| 8 | 0.02 | 0.04 |
| 9 | 0.025 | 0.06 |
| 10 | 0.02 | 0.065 |
| 11 | 0.025 | 0.070 |
| 12 | 0.025 | 0.065 |
| 13 | 0.02 | 0.060 |
| 14 | 0.03 | 0.06 |
| 15 | 0.02 | 0.05 |

The above examples provided as a means of illustrating the present invention and are not to be construed as limiting the invention, which is solely defined by the claims.

References

Bihoreau, N., et al., Eur. J. Biochem. 222: 41–48 (1994)
Chan, S. Y., U.S. Pat. No. 5,576,194 (1996)
Eis-Hubinger, A. M., et al., Thromb. Haemost. 76: 1120 (1996)
Mizrahi, A., J. Clin. Microbiol. 11–13 (1975)
Murhammer, D. W., et al.. Biotechnol. Prog. 6: 142–148 (1990)
Papoutsakis, E. T., Trends in Biotechnology (Tibtech) 9: 316–324 (1991)
Qi, Y-M. et al., Cytotechnology 21: 95–109 (1996)
Schmolka, I. R., J. Am. Oil Chemists' Soc. 54: 110–116
Schneider, Y-J., J. Immunol. Meth. 116: 65–77 (1989)
Wood, W., et al., Nature 312: 330–337 (1984)
Xu, D., et al., China J. Biotech. 11: 101–107 (1995)
Zhang, J., et al. Biotechnol. 33: 249–258 (1994)

We claim:

1. A method for production of recombinant Factor VIII from mammalian cells carrying the gene therefor, comprising culturing said mammalian host cells in medium free of plasma-derived protein and supplemented with polyols and copper ions.

2. The method of claim 1 wherein the polyol is Pluronic F-68 and is present in the medium at a concentration ranging from about 0.025 to about 0.2% by weight.

3. The method of claim 1 wherein the medium includes copper sulfate in an amount ranging from about 50 to about 800 nM.

4. The method of claim 1 wherein manganese ions are present in an amount ranging from about 1.5 to about 4.5 nM.

5. The method of claim 1 wherein ions containing molybdenum are present in an amount ranging from about 1.5 to about 4.5 nM.

6. The method of claim 1 wherein ions containing silicon are present in an amount ranging from about 75 to about 300 nM.

7. The method of claim 1 wherein chromium ions are present in an amount ranging from about 1.0 to about 4.0 nM.

8. The method of claim 1 wherein lithium ions are present in an amount ranging from about 120 to about 480 nM.

9. The method of claim 1 wherein said mammalian host cell is selected from the group consisting of baby hamster kidney cells, human embryonic kidney cells, and Chinese hamster ovary cells.

10. A cell culture medium for the production of recombinant Factor VIII comprising a basal medium free of plasma-derived protein and including a polyol and copper ions.

11. The medium of claim 10 including at least one trace metal selected from the group consisting of manganese, molybdenum, silicon, chromium and lithium.

12. The medium of claim 11 including insulin.

* * * * *